(12) United States Patent
Abulafia-Lapid et al.

(10) Patent No.: US 7,740,855 B2
(45) Date of Patent: Jun. 22, 2010

(54) INACTIVATED CD8+ T-CELLS FOR THE TREATMENT OF HIV INFECTION

(75) Inventors: Rivka Abulafia-Lapid, Yahud (IL); Henri Atlan, Jerusalem (IL); Irun R. Cohen, Rehovot (IL)

(73) Assignees: Yeda Research & Development Co. Ltd, Rehovot (IL); Hadasit Medical Research Services and Dev. Ltd, Jerusalem (IL)

( * ) Notice: Subject to any disclaimer, the term of this patent is extended or adjusted under 35 U.S.C. 154(b) by 0 days.

(21) Appl. No.: 11/290,682

(22) Filed: Nov. 30, 2005

(65) Prior Publication Data

US 2007/0122877 A1    May 31, 2007

(51) Int. Cl.
*A61K 39/00* (2006.01)
(52) U.S. Cl. .................................................. 424/184.1
(58) Field of Classification Search ........................ None
See application file for complete search history.

(56) References Cited

OTHER PUBLICATIONS

Abulafia-Lapid et al., T-cell vaccination against anti-CD4 autoimmunity in HIV-1 infected patients, Journal of Clinical Virology, 2004, 31S: S48-S54.*
Abulafia-Lapid et al., T-cell vaccination against anti-CD4 autoimmunity in HIV-1 subtypes B and C-infected patients-An extended open trial, Vaccine, 2005, 23: 2149-2153.*
Grube et al., An APC for every occasion: induction and expansion of human Ag-specific CD4 and CD8 T cells using cellular and non-cellular APC, Cytotherapy, 2004, 6(5):440-449.*
Atlan et al., Mechanisms of autoimmunity and AIDS : prospects for therapeutic intervention, Research in Immunology, 1994, 145(3):165-183.*
Schroers et al., Lentiviral transduction of human T-lymphocytes with a RANTES intrakine inhibits human immunodeficiency virus type 1 infection, Gene Therapy, 2002, 9:889-897.*
Minai et al., Activation via TCR or IL-2 receptor of a CD8 § suppressor T cell clone: Effect on IL-10 production and on proliferation of the suppressor T cell, Cytotechnology, 1994, 14:81-87.*
Senterfitt, CD8 Expansion Study of Immune-Based Therapy For KS Patients Planned At UCLA , Being Alive, 1993, http://www.aegis.com/pubs/bala/1993/BA930119.html.*
Bachmann MF, Oxenius A. Interleukin 2: from immunostimulation to immunoregulation and back again. EMBO Rep. Dec. 2007;8(12):1142-8.
PCR protocol by Kramer and Coen (2001) *Current Protocols in Molecular Biology*, John Wiley & Sons, Inc., 15.1.1-15.1.4.
Skeleton staining protocol by Selby, P. (1987) *Stain Technology*, vol. 62, No. 3, pp. 143-146.
Mixed lymphocyte-peptide culture by Jager, E. et al (1996) *Int. J. Cancer*, vol. 67, pp. 54-62.

* cited by examiner

*Primary Examiner*—Patrick J Nolan
*Assistant Examiner*—Nicole Kinsey White
(74) *Attorney, Agent, or Firm*—Frommer Lawrence & Haug LLP; William S. Frommer; Deborah L. Lu

(57) ABSTRACT

A method for the preparation of a T cell vaccine for the treatment of immunodeficient HIV-infected patients is described herein, based on the enrichment of autologous CD4-reactive CD8 T cells. Also described is a protocol for the implementation of T cell vaccination in immunodeficient HIV-infected, as well as a method of treatment, based on the T cell vaccine developed herein. Finally, kits for preparing the T cell vaccine as well as for implementing the protocol are also provided.

4 Claims, 4 Drawing Sheets

INACTIVATED CD8+ T-CELLS FOR THE TREATMENT OF HIV INFECTION

FIELD OF THE INVENTION

The present invention relates to the field of immunotherapy and AIDS. More specifically, the present invention relates to a new T cell therapeutic vaccine and a protocol for immunotherapy by T cell vaccination for HIV patients.

BACKGROUND OF THE INVENTION

All publications mentioned throughout this application are fully incorporated herein by reference, including all references cited therein. A full list of these publications is included at the end of the specification, immediately preceding the claims.

The hallmark of HIV infection and the eventual cause of AIDS is the progressive destruction of the CD4 T cell population. The in vitro cytopathic effects of HIV, with the CD4 molecule as its receptor and the gp120 molecule of the HIV envelope as its ligand, have led to the notion that HIV is the direct cause for the destruction of the CD4 T cell population [Lifson, J D. et al. (1986) *Science* 232:1123-1126; Casella, C R. et al. (1997) *Curr. Opin. Hematol.* 4: 24-31; Gandhi, R T. et al. (1998) *J. Exp. Med.* 187:1113-1122]. The inventors and others have previously suggested that additional mechanisms must account for the CD4 T cell decline during HIV infection [Grossman, Z. et al. (1993) *Clin. Immunol. Immunopathol.* 69: 1-13; Anderson, R W. et al. (1998) *JAIDS* 17: 245-252; Margolick, J B. et al. (1995) *Nat. Med.* 1:674-680; Quibin, L. et al. (2001) *JAIDS* 27:389-397] since the number of HIV infected cells at any stage of the infection is too small to account for the massive destruction of CD4 cells. One of the possible mechanisms that have been suggested is the killing of CD4 T cells by autologous CD8 T cells, with the CD4 molecules as self-antigens and targets for this autoimmune activity [Israël-Biet, D. et al. (1990) *Clin. Exp. Immunol.* 81:18-24; Zarling, J M. et al. (1992) *J. Immunol.* 144:2992-2998; Caporossi, A P. et al. (1998) *Virol. Immunol.* 11: 9-17]. Indeed, CD8 T cells of HIV-infected subjects were found to kill both HIV infected and non-infected CD4 T cells [Zarling (1992) id ibid.; Salemi, S. et al. (1995) *J. Exp. Med.* 81:2253-2257]. HIV infection could therefore be seen as an inducer for an autoimmune response against the CD4 molecule, leading to the destruction of the CD4 T-cell population [Lanzavecchia, A. (1995) *J. Exp. Med.* 181:1945-1948; Grant, M D. et al. (1994) *JAIDS* 7:571-579]. Such an autoimmune process could account for the persistence of CD4 T-cell leukopenia in patients despite complete or partial HIV viral suppression by highly active anti-retroviral treatment (HAART). Unfortunately, the proportion of such patients without sufficient immunological response is significant, reaching 50-60% in a number of reported series [Grabar, S. et al. (2000) *Ann. Intern. Med.* 133:410-410; Tarwater, P M. et al. (2001) *JAIDS,* 168-175; Pitrak, D L. et al. (2001) *AIDS* 15:1317-1319; Carcelane, G. et al. (2001) *Curr. Opin. Immunol.* 13:479-482; Kaufmann, G. R. et al. (2003) *Arch. Intern. Med.* 163:2187-95].

T cell vaccination (TCV) has been studied in experimental animals [Ben-Nun, A. et al. (1981) *Nature* 292:60-61; Holoshits, J. et al. (1983) *J. Immunol.* 131:2810-2813; Lider, O. et al. (1988) *Science* 239: 181-183] and lately has been used clinically to induce the down-regulation of autoimmune diseases such as multiple sclerosis [Van Laar, J M. et al. (1993) *J. Autoimmunity* 6:159-167; Haffler, D A. et al. (1992) *Clin. Immunol. Immunopathol.* 62: 307-317; Zhang, J. et al. (1993) *Science* 262: 1451-1454; Zhang, J. et al. (2000) *J. Immunol.* 164:4011-4017]. In all these instances, it was designed to raise an immune response in the host against the autologous effector cells that are causing the pathological changes responsible for the autoimmune disease. When successful, TCV has resulted in the suppression of these effector cells by the host response to the T cell vaccines, and the disease was either prevented or ameliorated. Based on the hypothesis that an autoimmune process takes place during HIV infection, Atlan and colleagues have suggested that autologous anti-CD4 T cells might be used as vaccines to down-regulate anti-CD4 autoimmunity in HIV-infected patients [Atlan, H. et al. (1993) *Immunol. Today* 14:200-202; Atlan, H. et al. (1994) *Res. Immunol.* 145: 165-183; Atlan, H. and Cohen, I R. (1996) *Immunology of HIV Infection.* New York: Plenum Press, Ch. 28].

Despite all the hypotheses that were raised in this respect, no studies have been done so far, at the clinical level, in order to verify the cellular origin of the immunodeficiency observed in HIV-infected individuals. The present study is the first of its kind in identifying one of the main causes of CD4+ T-cell depletion during HIV infection. The inventors investigated whether an autoimmune reaction towards CD4 is present in HIV infected patients, in comparison to controls. CD4-recognizing CD8 cells were found circulating and functional in HIV-infected patients, and such reactivity was evidenced in most of the HIV infected individuals. Thus, the present inventors propose and prove possible the generation and the use of inactivated CD4-specific CD8 cells as a tailor-made vaccine for treating HIV-induced immunodeficiency. In this context, the inventors went one step further and performed an open trial of the TCV developed herein in HIV-infected individuals. Results are summarized in Example 1 below. Based on the encouraging results of this study, the inventors developed a general outline for a T-cell vaccination protocol.

Thus, it is an object of the present invention to provide a method for preparing T cell vaccines tailored for immunodeficient patients, particularly when the immunodeficiency is consequent of HIV infection. The invention also provides a method of treatment of an auto-immune process induced by HIV infection. To a larger scale, the invention provides a T-cell vaccination protocol, based on the tailored-made T cell vaccines prepared from HIV-infected individuals.

SUMMARY OF THE INVENTION

Thus, in a first aspect, the present invention provides a method of preparing a T cell vaccine for a patient suffering from HIV-induced immunodeficiency, wherein said vaccine comprises a population of autologous cells enriched with inactivated CD8+ cells that are reactive to CD4+ cells, said method comprising the steps of:

a) Obtaining peripheral mononuclear blood cells (PMBC) from said patient;

b) Culturing said autologous cells in the presence of a stimulating factor;

c) Expanding said autologous cells in the presence of IL-2;

d) Culturing said expanded autologous cells in the presence of irradiated CD4-pulsed antigen presenting cells (APCs);

e) Inactivating said autologous cells in the presence of an inactivating factor;

f) Washing said autologous cells and ressuspending the same in injection-grade saline solution; and g) Optionally freezing aliquots of between $10^6$-$10^8$ cells in liquid nitrogen.

In one embodiment, the method of the invention may provide the preparation of a substantially pure cell population enriched with inactivated autologous CD8+ cells that are reactive to CD4 molecule (CD4+ cells), in which case step (d) above is repeated for between 4 to 8 times.

In a second aspect the present invention provides a protocol for T cell vaccination of immunodeficient HIV-infected patients, comprising the steps of:
a) Recruiting the subjects to be part in the protocol, wherein said recruitment consists of: (i) having potential subjects to be included in the protocol, respond to a questionnaire consisting of questions regarding demographics and personal medical history; (ii) screening the subjects with respect to inclusion and exclusion criteria, wherein inclusion criteria involve positive cell proliferation assay to CD4 molecule and optionally preferably no change of anti-retroviral treatment for at least the last 6 months before enrolling in the protocol, and exclusion criteria consist of any one of the criteria selected from the group consisting of: use (at the time of enrolling in the protocol) of anti-neoplastic drugs, use (at the time of enrolling in the protocol) of immunosuppressive drugs, use (at the time of enrolling in the protocol) of chronic systemic glucocorticoid therapy, pregnancy, lactation, liver disease, serum creatinine higher than 1.8 mg/dl or creatinine clearance lower than 30 ml/min and legal incapacity; (iii) following the screening, applying at least 3 of the following laboratory tests in the subjects that were included in the protocol: blood T cell subsets; plasma HIV-1 RNA load, FACS analysis for activation markers, specific anti-CD4 immunity, skin tests for delayed hypersensitivity to recall antigens, and specific immune response to recall antigens such as tetanus toxoid, candida, influenza, etc.;
b) Administering a therapeutically effective amount of an anti-CD4 autoimmune T cell vaccine, wherein said vaccine consists of a pool of PMBC cells enriched for autologous CD8+ cells, wherein said PMBC cells originate from the same subject to whom said vaccine is administered, and were cultured in the presence of a T cell stimulating agent, followed by expansion in the presence of IL-2 and re-stimulation in the presence of CD4-pulsed antigen presenting cells, followed by killing of the CD8+ anti-CD4 cells, or a composition comprising said vaccine, to said subject; and
c) Evaluating the response to said vaccine by said subject, wherein said evaluation involves: (i) clinical follow up, consisting of analysis of viral load and plasma CD4 counts; (ii) immunological follow-up, consisting of anti-clonotypic assay, anti-CD4 autoimmunity assay, cytotoxicity assay and anti-recall antigens assay.

In a further aspect the present invention provides a method of treatment of an autoimmune process induced by HIV infection, comprising administering a therapeutically effective amount of a T cell vaccine, wherein said vaccine consists of a pool of PMBC cells enriched for autologous CD8+ cells anti-CD4, wherein said PMBC cells originate from the same subject to whom said vaccine is administered, and were cultured in the presence of a T cell stimulating agent, followed by expansion in the presence of IL-2 and re-stimulation in the presence of CD4-pulsed antigen presenting cells, followed by killing of the CD8+ anti-CD4 cells, or a composition comprising thereof, to a subject in need.

In this respect, the present invention also provides a method of treating AIDS, said method comprising the above-described method combined with anti-retroviral treatment.

In an even further aspect the present invention provides a composition comprising as effective agent an anti-CD4 T cell vaccine, wherein said vaccine consists of a pool of PMBC cells enriched for autologous CD8+ cells, wherein said PMBC cells originate from the same subject to whom said vaccine is administered, and were cultured in the presence of a T cell stimulating agent, followed by expansion in the presence of IL-2 and re-stimulation in the presence of CD4-pulsed antigen presenting cells for several rounds, followed by inactivation of the autologous CD8+ anti-CD4 cells.

In yet another aspect the present invention provides a method of treating AIDS, said method comprising the method of treatment as defined in claim 3, combined with anti-retroviral treatment.

Finally, the present invention provides two kits: one for preparing a T cell vaccine against anti-CD4 autoimmune T cells, wherein said vaccine is to be used as therapy in subjects suffering from HIV infection-induced immunodeficiency, and wherein said kit comprises:
a) Means for obtaining PMBC;
b) Means for cultivating PMBC;
c) Stimulating factor, preferably PHA;
d) IL-2;
e) Irradiated CD4-pulsed antigen presenting cells;
f) A fixating agent, preferably glutaraldehyde;
g) Glycine;
h) Subcutaneous injection-grade saline; and
i) Manual with instructions on how to prepare the T cell vaccine.

The second kit is intended to supply the elements necessary for the implementation of the above-described protocol for T cell vaccination of immunodeficient HIV-infected patients. Said kit comprises the same tools as described above, necessary for preparing a T cell vaccine against autologous CD8 cells which recognize CD4 cells and further comprises instructions for implementing the above-described protocol. As part of the instructions for implementing the protocol it is understood all the forms and standard procedures that should be followed by both the medical personnel implementing the protocol and the patients enrolled in the same.

BRIEF DESCRIPTION OF THE FIGURES

FIG. 1A: CD4 T-cell numbers following TCV in two patients. The absolute numbers of peripheral blood CD4 T cells were measured during the 2 years both before (- - -) and after (---) the initiation of TCV. The vertical line represents the time point of the initial TCV (first day of injection). The arrows represent the time points of the TCV injections. Linear regression slopes of CD4 T-cell numbers were calculated for each of the patients, before and after TCV. The plasma viral loads are indicated under the slopes by numbers (copies/ml blood); BD indicates below detection.

FIG. 1B: T-cell proliferative responses to rCD4 and to Tetanus Toxoid following TCV. T-cell proliferative responses were measured before and 2 years after the onset of TCV by $^3$H-thymidine incorporation assay. The results are presented as the S.I. Patients: P1 (♦), P2 (■), P3 (▲), P4 (*), and P6 (●).

Patients: P1 (♦ blue), P2 (● black), P3 (■ pink), P4 (*), P5 (▲ green), P6 (○ light blue) and P7 (yellow).

Figure 4:
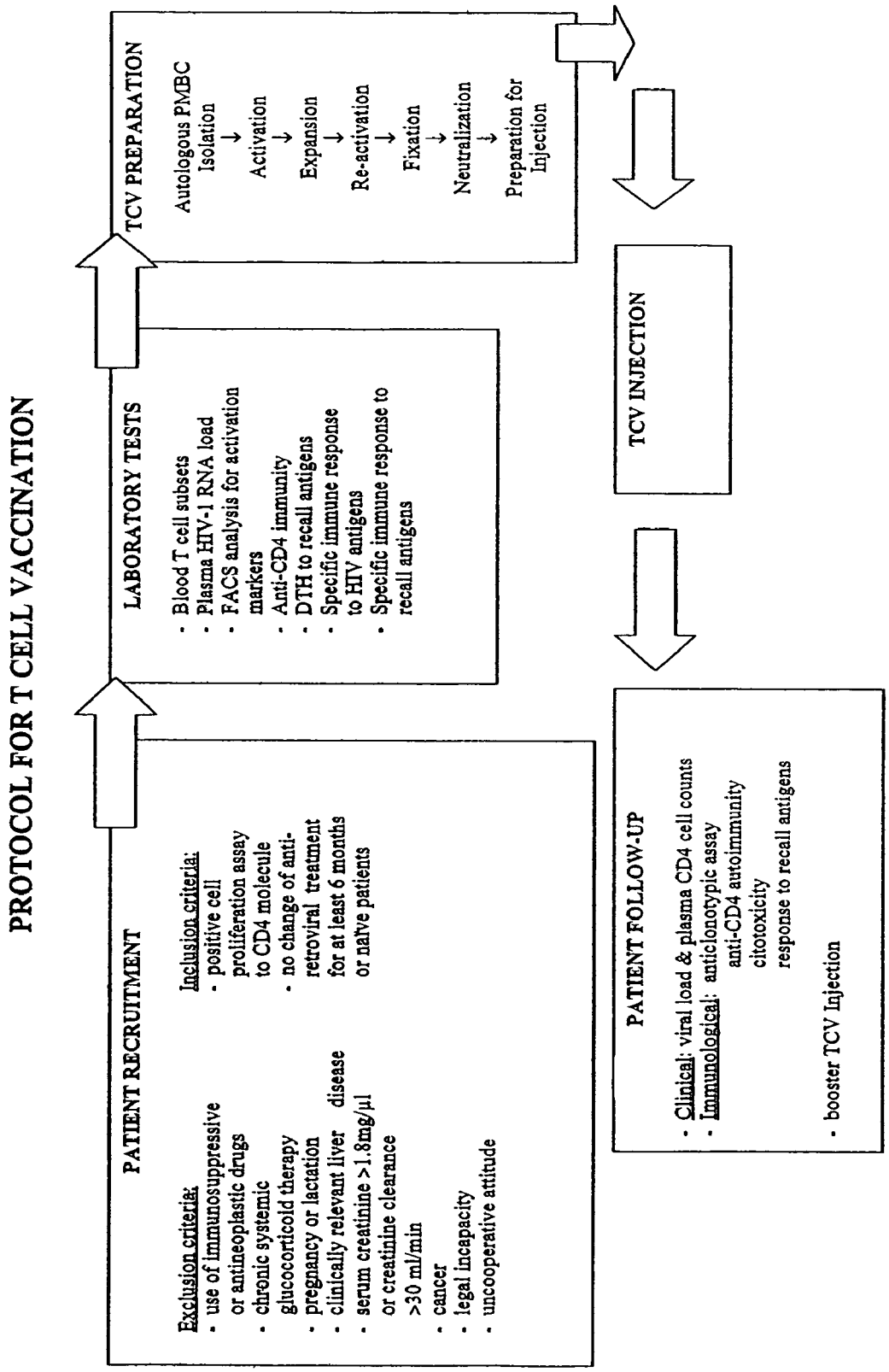

FIG. 4: Flow-chart of T-cell vaccination protocol for HIV-1 seropositive patients.

DETAILED DESCRIPTION OF THE INVENTION

The present inventors have developed a T cell vaccine for the treatment of immunodeficiency triggered by HIV-infection. The vaccine is based on the principle that HIV-infected individuals suffer from immunodeficiency as a result of CD4+ T cell destruction by activated autologous anti-CD4 T cells. During HIV infection, CD4+ T cells become the target of CD8+ T cells. The goal of the present inventors was to find means to eliminate the circulating CD4-recognizing CD8 T cells, thus increasing the number of circulating CD4 cells, and in this way treating the immunodeficiency.

More specifically, the present inventors developed a method of preparing a T cell vaccine for treating patients with HIV-induced immunodeficiency, wherein said vaccine comprises a population enriched with inactivated autologous CD8+ cells that are reactive to CD4+ cells. As detailed in the Examples, the method consists of obtaining peripheral mononuclear blood cells (PMBC) from the patient to be treated, culturing said cells in the presence of a stimulating factor for between 2 and 4 days; expanding said cells in the presence of IL-2 for between 13 and 18 days; culturing said expanded cells in the presence of irradiated CD4-pulsed antigen presenting cells (APCs) for between 7 and 9 days; inactivating said cells in the presence of an inactivating factor; preparing the cells in a solution containing between about $0.5-2 \times 10^7$ cells/ml, preferably $10^7$ cells/ml, dissolved in an FDA-approved saline injection solution. In order to have additional vaccines for applying boosters to the patients, aliquots of the vaccine should be frozen for future use. Another batch of vaccine from the same patient may be prepared in the beginning of the treatment, in case the number of cells obtained after the first preparation is not sufficient for several boosters. However, in this case, the second preparation should be done very soon after the first injection, otherwise, the treatment starts having its effect, and the patient will stop producing said CD4-recognizing CD8 cells.

In the present Examples the inventors used phytohemmaglutinin (PHA) for the stimulation step, but other stimulators such as anti-CD3, or anti-CD3 in combination with anti-CD28, or IL-2, or PHA+IL2 may also be used. The step of PHA stimulation, or augmentation, was introduced by the present inventors for the preparation of this TCV after several failures of trying to expand the autologous CD8 population directly by exposure to the antigen, without first stimulating the cells. Thus, in the present method, the frequency of autologous autoimmune cells is first increased, to only then be exposed to IL-2. Exposure of the cells to IL-2 is preceded by 36-48 h of starvation.

With regards to the expansion, since the goal is to expand the CD8+ cells present in the PBMC pool, IL-2 is the preferred interleukin used. After the expansion step, the cells should be followed and observed under the microscope, before proceeding to the next step. Before being exposed to the APCs, the enriched cells should be entering into rest phase and only then be exposed to the antigen.

The next step involves expanding specifically the population of CD8 cells that recognize CD4. Thus, irradiated CD4-pulsed antigen presenting cells (APCs) are introduced to the culture. The APCs used are autologous PMBCs which were pulsed with CD4 antigen, preferably human recombinant CD4 antigen, as described in Experimental Procedures below. Alternatively, the autologous CD8 cells may be exposed directly to CD4 antigen for expansion, wherein said antigen is immobilized or solid phase presented antigen. CD4 antigen or peptides or derivatives thereof should preferably be human, and recombinant. Enrichment of the CD4-recognizing CD8 cells depends on this last step, which essentially promotes augmentation of the autologous CD8 memory cells. Thus, this step may be repeated several times for enhancing the number of said autologous CD8 cells. If desired, the population of CD4-reactive autologous CD8 cells may be further selectively purified, through any cell selection means. Further to the step of CD8 memory cell augmentation (with or without the optional purification), and before injection, the then enriched population of CD4-recognizing CD8 cells is inactivated. In the present study, the inventors inactivated the cells with glutaraldehyde, but other agents may be used as well, such as other fixing solutions like formaldehyde or paraformaldehyde. Alternatively, these cells may be irradiated (6,000-7,000 rads) prior to injection. Fixation is preferred since it also inactivates any viral particles that might have been carried on from the sample obtained initially from the patient, while also inactivating any other contaminants.

Further to the step of fixation, which is usually done for 5 minutes (see Experimental procedures), the fixating solution should be neutralized in the presence of glycine, for around 20 minutes. Neutralization is followed by several rounds of washes with saline, usually at least three times, and in the final wash the cells are prepared to a final concentration of 10,000,000 cells/ml, in FDA-approved saline solution, injection grade.

It is important to note that by CD4 molecule it is also meant any functional fragments, analogs or derivatives of CD4 which may also be used for exposure to CD8 cells. By "functional fragments" of the CD4 molecule it is meant any fragment that may be recognized by the CD4-recognizing autologous CD8 cells. A "variant" of such molecule is meant to refer to a naturally occurring molecule substantially similar to either the entire molecule or a fragment thereof. An "analog" of a molecule is a homologous molecule from the same species or from different species.

The vaccine may be administered as is, or in the form of a composition comprising as active agent said autologous, tailor-made T cell vaccine. Such a composition may further optionally comprise additional active agents that may be part of the treatment of each specific patient. Thus, for example, said composition may further optionally comprise antibiotics, vitamins, etc.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein.

Most importantly, all the procedures for preparing the T cell vaccine were carried out in a laboratory of P3 level of isolation, according to FDA standards and under serial conditions.

The prepared pool of autologous CD4-recognizing CD8 cells is then injected subcutaneously in the patient (from whom the PMBC cells were obtained), with a maximum of 1.5 ml/injection, preferably 1 ml, containing $10^7$ cells, triggering an immune response.

Upon injection, the immune system is recruited to the area. Similarly to the subcutaneous injection of a vaccine comprising a weakened bacteria, or an inactivated virus, the injection of the autologous CD4-recognizing CD8 cells will trigger an immune response. The immune cells will recognize the injected (autologous) cells as foreign (or antigenic), and start the process of learning and teaching the body to recognize these cells as foreign. Once the body recognizes these cells as foreign, it will form a response against these cells. In this manner, not only the injected cells are recognized as foreign, but also any CD4-recognizing CD8 cells that may be present in the circulation are now viewed by the autologous immune system as foreign, and shall also be destroyed.

Since T cell vaccination (in general) is still in its infancy, and in particular for the present condition where this is the first attempt to introduce it in the treatment of AIDS patients, it is important to closely follow up its more wide-scale implementation. Therefore, the present inventors have also proposed a standardized protocol (Example 2 and FIG. 4), which should be followed by centers of reference for AIDS treatment interested in implementing the herein described T cell vaccination.

This protocol has been prepared and applied following all the steps necessary for phase II/III multi-site clinical trials, including all the forms and standard procedures that are necessary for FDA approval. In this respect, Standard Operating Procedure, Investigator Brochure, Data Monitor, Clinical Regulatory Authority, Master Manufacturing Instructions, Clinical Record Form, and Quality Control records were followed. All these brochures are part of the instructions for implementing the protocol described in the invention. The efficacy and practicability of the herein described T cell vaccine and vaccination is shown in Example 1 below, which describes an initial trial of T-cell vaccination. Thirteen of the 43 HIV infected patients that were selected and screened for TCV manifested T-cell reactivity to the CD4 molecule. Their auto-reactivity to CD4 appeared to be independent of the plasma HIV viral load, since no correlation was found between the viremia or HIV type (Table 1) and the in vitro T-cell proliferative response to CD4 (correlation coefficient=0.2817 and 0.2298, respectively).

It is important to note that there were several reasons to believe that the TCV herein described would not be feasible for treating immunosuppressed HIV-infected individuals. It would have been reasonable to expect that cells obtained from such individuals would be difficult to stimulate or grow in culture, due to their origin (from immunosuppressed individuals). The present inventors overcame this limitation by activating these cells, which are memory cells, in the initial PHA treatment. Furthermore, it was not obvious that said cells would respond to CD4 stimulation, since they did not respond to gp120 stimulation (see Table 1 below). Another possible hindrance would have been the aggravation of viral load upon vaccination. Theoretically, the proposed treatment could worsen the viremia. However, this result was not observed in the treated patients. Lastly, one additional pessimistic prediction for the proposed TCV would be that viruses that would have been present in the initial sample of cells harvested from the patient would mutate, becoming more aggressive and virulent, and then be re-introduced into the patient, worsening the condition. However, this latter possibility has been impeded due to the fixation of the cells with glutaraldehyde, which also inactivates viral particles.

Thus, against all odds, Example 1 below shows that the herein presented T-cell vaccine is feasible, and strongly indicates that the T cell vaccination protocol provides a promising future in terms of treatment and follow-up of HIV-infected individuals.

Most importantly, the results of Example 1 may be summarized as follows. Firstly, T-cell vaccination in HIV-infected patients showed to be feasible, since it was possible to raise a sufficient number of autologous T cells to fashion a vaccine, even in persons with detectable viremia. Secondly, the resulting vaccines were composed of T cells enriched for CD8 cells that produced more IFN-$\gamma$ than IL-10, suggesting that they were T1-type cells (Table 2). Thirdly, some of the subjects appeared to respond to the vaccination by a reduction in anti-CD4 autoimmunity (FIG. 1B and data not shown) and by a raise in absolute numbers of peripheral blood CD4 T cells. Except for three patients (P5, P10 and P12), all patients showed a change above 50% (median 70%; Table 3A and FIG. 1A). This was not seen in a comparable group of non-vaccinated patients followed for the same period of time, where only two patients (CP3 and CP6) showed a change above 50% (median 27%; p=0.007; Table 3). Fourthly, in no instance was there an aggravation of the patients' condition, in particular any decrease in CD4 cell numbers was observed. In two patients (P2 and P12), the viral load was highly unstable before and after TCV, but a significant increase in CD4 cell counts from 400 to 700 was observed two years after vaccination (Table 3A).

Finally, as mentioned above, some patients entered the study with relatively high viral loads, and the T cell preparations used as vaccines still contained appreciable numbers of CD4 cells. Nevertheless, no virus could be detected in the supernatants of the cell cultures. This suggests that some of the T cells in the culture may have had anti-HIV activity in vitro. However, it is unlikely that the vaccination produced any undesirable immune response against HIV-specific cytotoxic T lymphocytes (CTLs), since there was no significant clinical deterioration following vaccination. With the exception of patient P2 discussed above, none of the patients showed an increase in viral load after TCV. Actually, two vaccinated subjects showed a significant decrease in their viral load two years after TCV, indicating, at least, that TCV did not decrease the efficacy of the ongoing antiviral therapy. How HIV infection may activate autoimmunity to CD4 is unknown, but conceivably, it could be related to an immunogenic alteration of the CD4 molecule following the binding of gp120 to CD4 [Morrow W J. et al. (1991) *Clin Immunol. Immunopathol.* 58:163-180; Salemi (1995) id ibid.; Caporossi (1998) id ibid.; Lanzavecchia (1995) id ibid.], and/or to the abnormal state of activation of the immune system in HIV-infected persons [Leng, Q. et al. (2001) *JAIDS.* 27:389-397; Salemi (1995) id ibid.]

It could be argued that the increase of CD4 following TCV was not related to the vaccination itself, but was rather the long-term, albeit delayed, outcome of HAART. However, the observations in the control group of unvaccinated patients suggest that TCV was indeed responsible for the CD4 increase. The increase in CD4 T-cell counts in the TCV treated subjects and the lack of toxicity are encouraging and support the idea that this treatment is indeed appropriate to be implemented routinely in Centers of Reference.

In conclusion, this study shows that TCV against anti-CD4 cells in HIV-infected patients is feasible and safe with no adverse effects. Cells from patients with both HIV subtypes B and C manifested the same anti-CD4 autoimmunity and responded the same to TCV.

The T cell vaccination proposed herein is a good candidate to be combined with anti-retroviral therapy, such as HAART. Moreover, this TCV shall be applicable to all 10 types of HIV viruses (A-J). Subjects infected with types B and C were investigated by the present inventors, but it is reasonable to expect that subjects infected with the other subtypes would be responsive as well.

"T-cell proliferation" as used herein means the number of T-cells produced during the incubation of T-cells with the antigen presenting cells, with or without antigen.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Experimental Procedures

Subjects

Forty-three HIV-infected patients were recruited at the Department of Microbiology, Hadassah Ein Kerem University Hospital (Jerusalem, Israel) and at the Kaplan Hospital AIDS Center (Rehovot, Israel). From these, thirteen were included in the open trial (Table 1). Their CD4 T cell numbers ranged from 172 to 531 cells/µl (median 327) and their plasma viral loads (Amplicor® (PCR analyzer), Hoffman-LaRoche, Basel, Switzerland) from <400 to 37,000 copies/ml (median 2200) (Table 1). The study was approved by the Ethical Committees of the Hadassah Ein Kerem University Hospital and the Kaplan Medical Center. Before entering the study, all patients signed an informed consent. All patients were receiving HAART. Blood was also obtained from 20 HIV-seronegative, healthy donors, through the Tel-Hashomer Central Blood Bank (Tel Aviv, Israel), to serve as controls (data not shown). In addition, seven HIV-infected patients (CP1-CP7), three males and four females, receiving HAART (median four years) were used as historical controls during at least four years of observation. Their CD4 T-cell numbers ranged from 108-224 cells/µl (median 190, 17%), and their plasma viral loads from <400 to 8,300 (median 3,890).

T-Cell Proliferation Assay

Peripheral blood mononuclear cells (PBMC) were isolated by density centrifugation on Ficoll Paque® (Ficoll 400 and diatrizoate sodium solution) (Pharmacia® Biotech, Uppsala, Sweden) from 30-40 ml of heparinized venous blood, obtained from patients or from the Blood Bank (see above). Cells were cultured in RPMI 1640 medium (Biological Industries Ltd., Beit Haemek, Israel), supplemented with 10% fetal calf serum (FCS) (Gibco BRL, Buffalo, N.Y., USA), 1% sodium-pyruvate, 1% L-glutamine, 1% Penicillin/Streptomycin (10,000 U/ml/10,000 mg/ml) (Seromed, Berlin, Germany) and 2% Hepes (1M, pH7.3) (Biological Industries, Beit Haemek, Israel). Specific cell proliferation was assayed by $^3$H-thymidine incorporation, as described previously [Abulafia-Lapid, R. et al. (1999) *J. Autoimmunity* 12: 121-129]. The antigens used were soluble recombinant human CD4 and HIV-1 gp120 proteins (2-5 µg/ml each), expressed in baculovirus (Intracell Corp., Cambridge, Mass., USA, or other source), tetanus toxoid (5 µg/ml, Connaught Lab. Inc., PA, USA, or other source), candida (10 µg/ml, Hollister-Stier®, Toronto, Canada, or other source) (data not shown, but discussed), and PHA (0.3 µg/ml, Murex® Diagnostics Ltd., Dartford, UK, or other source). The cells were plated in 96-well round bottom microplates (Falcon™, Lincoln Park, N.J., USA), at a cell concentration of $2 \times 10^5$ cells/well in medium, with or without the test antigens or mitogen. The plates were incubated at 37° C. in a 5% $CO_2$ humidified incubator for 7 days. On day 6, the cells were labeled overnight with 1 µCi/well of $^3$H-thymidine and counted in a Matrix 96 β-counter (Packard, Meriden, Conn., USA). The results of the proliferation assays are presented as stimulation indexes (S.I.). A stimulation index of above 2 was considered as a positive response. This value was chosen for two reasons: (1) the minimum concentration of CD4 was used (2 µg), and (2) the low frequency of these cells as a result of immuno-suppression. Statistical analysis was performed using the InStat 2.01 computer program, and P values using the Mann-Whitney non-parametric test.

Figure 1A:
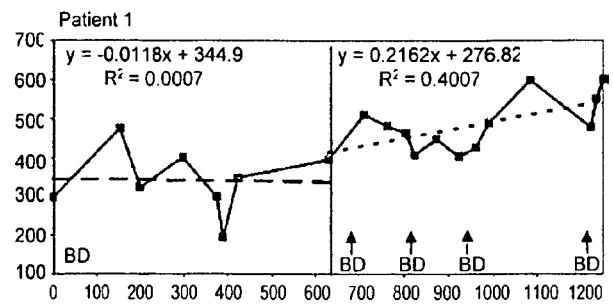
FIG. 1A-B.
Figure 1A:
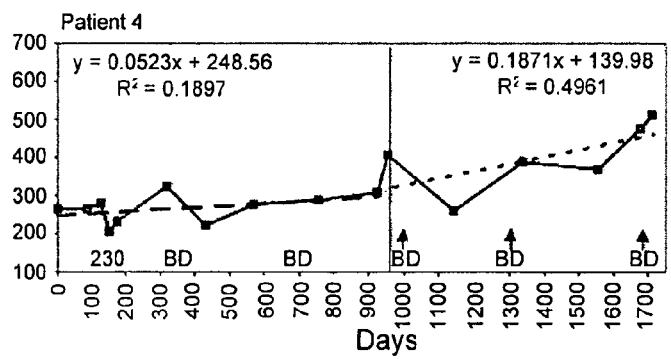
Figure 1B:
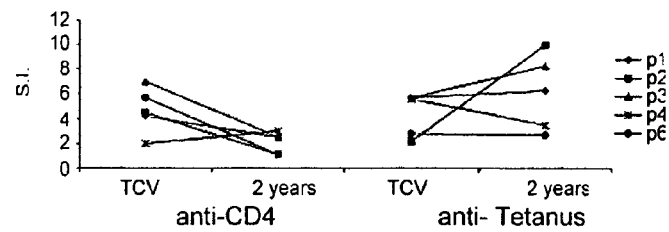
Figure 2:
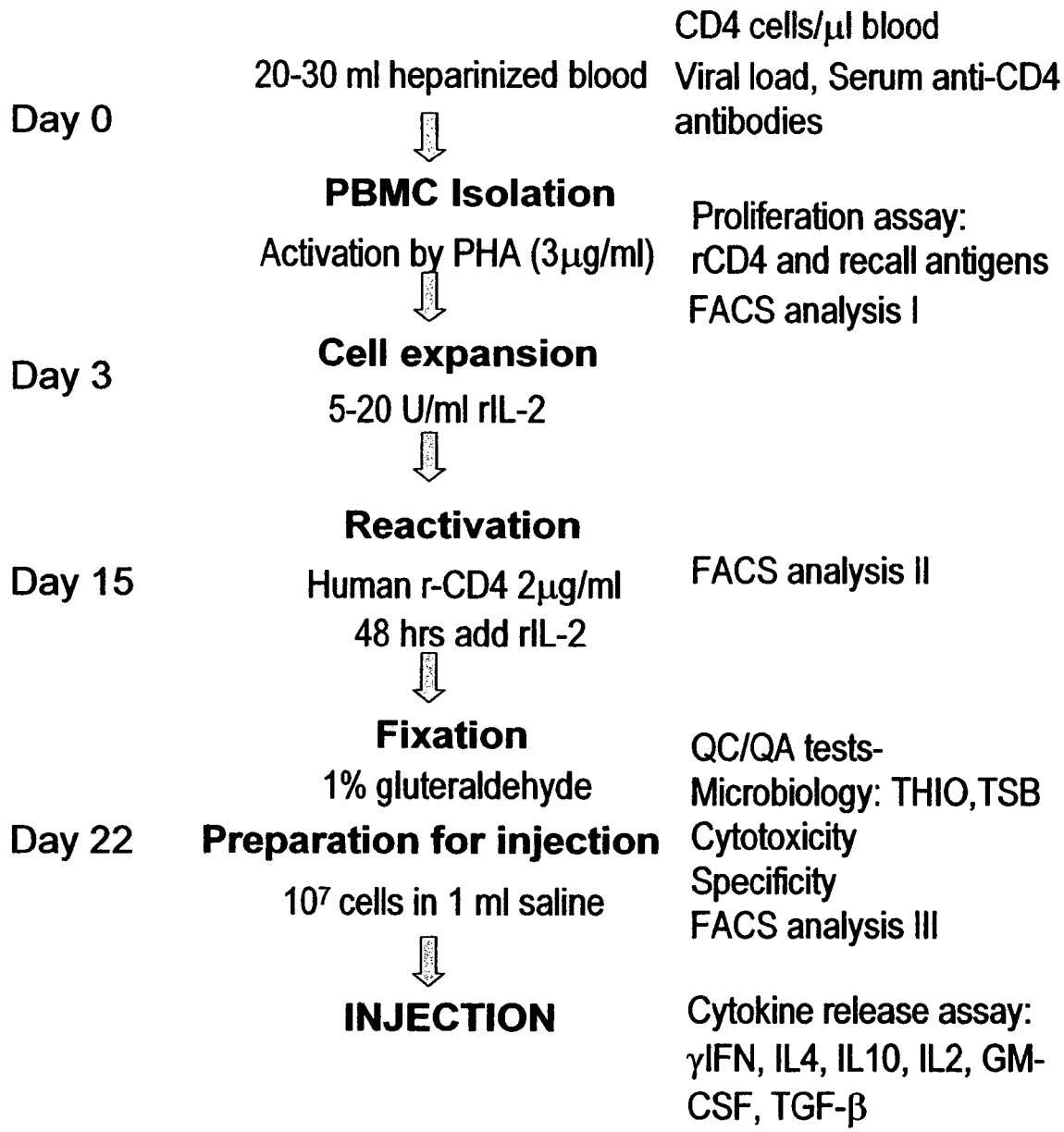
FIG. 2: T cell Vaccine Preparation
Figure 3:
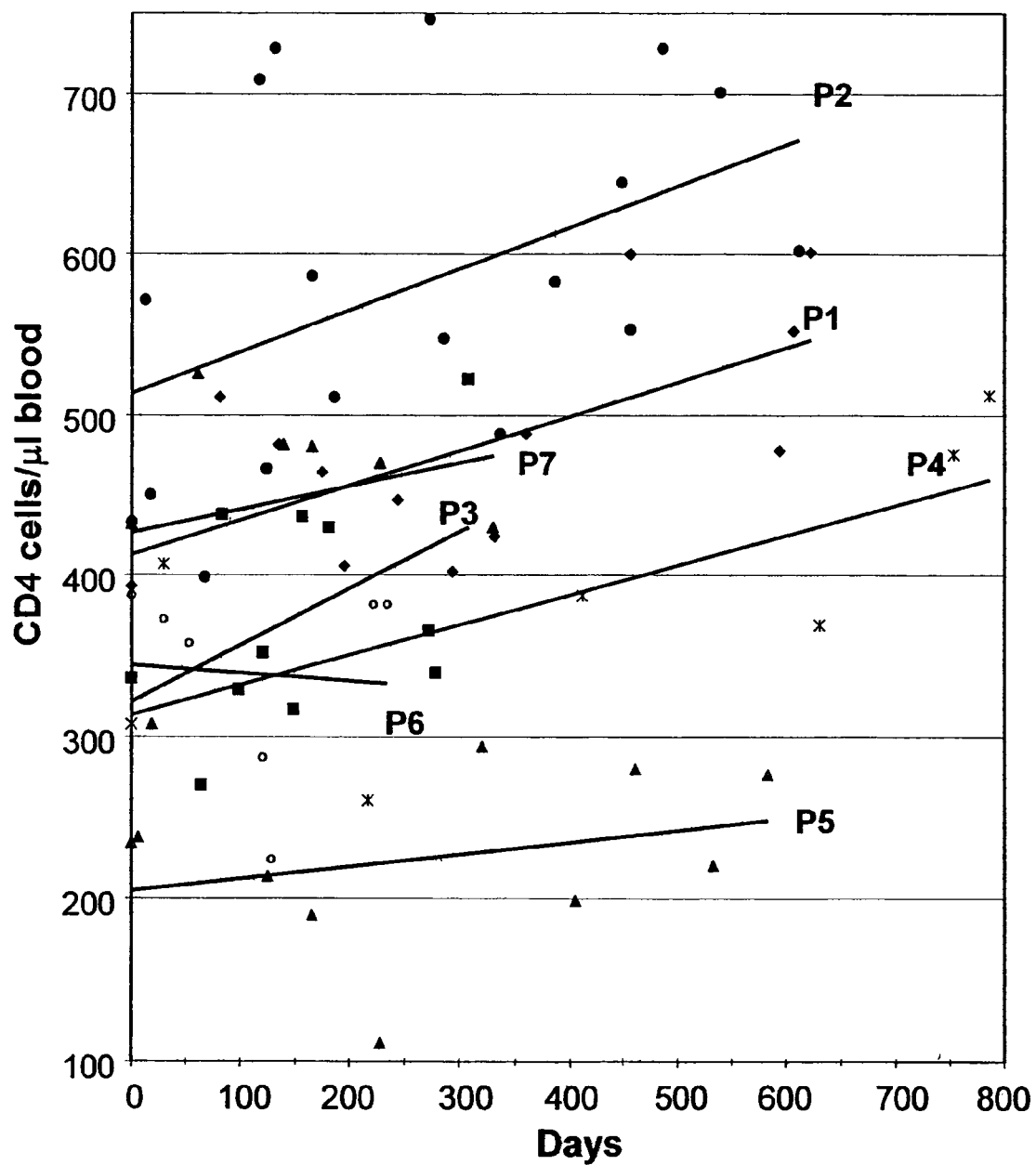
FIG. 3: Plasma CD4 T cell numbers following T cell vaccination. The graph shows the absolute numbers of peripheral CD4 T cells that were measured during between one to two years following the T cell vaccination. Linear regression slopes of CD4 T cell numbers were calculated for each of the patient's scattered points.

Protocol for the Preparation of the T Cell Vaccine (TCV)

rCD4-reactive T cells were generated from 30-40 ml of blood obtained from each patient for vaccine preparation. All cultures were performed according to the procedures required for the preparation of biological products to be used in humans. Briefly, PBMC were isolated from the blood of each of the patients (first sample), cultured with 3 µg/ml phytohemaglutinine (PHA) (Murex® Diagnostic Ltd., England) for 3 days, and expanded with 5-20 U/ml recombinant interleukin-2 (rIL-2) (Boehringer® Mannheim GmbH Mannheim, Germany) for 11 days. The cultures were re-stimulated on day 14, with irradiated rCD4-pulsed antigen presenting cells (APCs) as described (see "Protocol for preparation of APC" below) [Zhang et al. (1993) *Science* 262:1451-4; Zhang and Raus, ed. (1995) *T-cell vaccination and autoimmune disease*. New York Landes Co.], and were further grown for another seven days. On day 21, the cells were inactivated for 5 minutes at room temperature with 1.0% glutaraldehyde (Sigma® Chemical Co., St Louis, Mo., USA) and prepared for injection. Aliquots of $10 \times 10^6$ CD4 reactive-T cells were frozen in liquid nitrogen, to be used later for second and third booster vaccinations, at two to six month intervals (FIG. 1A). For pure lines of anti-CD4 cells, several rounds of rCD4 re-stimulation are necessary, preferably between 4 to 8 rounds.

Protocol for Preparation of CD4-Pulsed APCs

The CD4-presenting APCs used for re-activating the enriched population of autologous CD8 cells must be freshly prepared, and, in order to avoid histocompatibility problems, must also be autologous. Thus, a second blood sample was collected from the patients around 14 days (+2-3 days) after collecting the first sample, or, on the day the enriched CD8 cells were exposed to the antigen. Briefly, the preparation of APCs was as follows. PBMCs were isolated by density centrifugation on Ficoll Paque® (Ficoll 400 and diatrizoate sodium solution) as described above, from 30-40 ml of heparanized venous blood from the same patient. The cells were then concentrated to 10 million cells/ml in RPMI 1640 medium with 10% fetal calf serum (FCS) as described above (in 15 ml polypropylene test tube). 20-50 µg/ml of recombinant human CD4 was added and the cells incubated for 3 hours at 37° C. in a 5% $CO_2$ humidified incubator. The cover of the tube was not tighten all the way, so that air could penetrate the cells from the $CO_2$ incubator, and the cells were shaken every 15 minutes. Further, the volume completed to 14 ml with RPMI 1640 medium +10% FCS. Cells were counted using the Tripan blue exclusion method with a hemocytometer, and centrifuged at 1800 rpm for 10 min (with "Brake" on). The supernatant was then discarded and the pelleted cells re-suspended to a dilution of 10 million cells/ml. The cells were irradiated at 7,000 rad, and re-suspended to a dilution of 1 million cells/ml. This APC cell preparation was then added to the expanded T cells at a ratio of 1:1. All the steps were handled in sterile conditions.

Selection of CD4-Reactive CD8 Cells

In order to increase the purity of the CD8 population to be injected to the patient, these cells may be selected by any suitable means for enriching cell populations, like FACS or through magnetic beads.

The protocol for selection with magnetic beads is as follows:

Dynabeads® (Dynal® Biotec ASA, Smestad, Norway) should be washed before use. The washing procedure is facilitated by the use of a magnetic device. The Dynabeads® are resuspended in the vial, and the desired amount transferred to a washing tube. 1-2 ml of washing buffer are added and the beads re-suspended. The washing tube is placed on a magnetic particle concentrator (Dynal® MPC) for 1 min and the supernatant discarded. Washing should be repeated and the washed beads resuspended in a volume equal to the original volume.

Depletion of CD4+ T cells: Prepare the cell sample. For PBMC suspensions, resuspend cells at $0.5-5 \times 10^7$ total cells/ml PBS/2% FCS. Add Dynabeads® (magnetic separation beads) CD4 according to the estimated number of target cells in the sample using $\geq 4:1$ bead to target cell ratio and $\geq 2 \times 10^7$ beads/ml (>144 µl). Incubate for 30 min at 4° C. or at 37° C. on an apparatus which allows both gentle tilting and rotation. Add PBS/2% FCS to a final volume of 5-10 ml. Place the test tube in the Dynal® MPC for 2-3 min to collect the bead rosetted cells. Transfer the CD4+ T cell depleted supernatant into a fresh tube for further studies. 99% depletion is usually obtained.

T Cell Vaccination and Patient Follow-Up

Trained medical personnel administered vaccinations in an AIDS clinic to thirteen HIV-infected patients: P1-P13 (12 males and 1 female; median age 41) (Table 1). The effects of the TCV were evaluated on the basis of clinical, immunological, and virological assessments, before, during and following the first injection for one to two years. Seven HIV-infected patients receiving HAART (3 males and 4 females; median age 53) (Table 3B) were not vaccinated and were followed as controls for changes in CD4 counts in the absence of TCV. The clinical follow-up of the patients consisted of a complete physical examination and blood tests including a complete blood count and biochemistry (liver function and renal function). Following each injection, the patients were monitored at the clinic for two hours for any immediate side-effects, and remained under close surveillance by the treating physician for an additional seven days to record any adverse events. Adverse effects were monitored according to the WHO protocol. The immunological follow-up consisted of: a) total lymphocytes and T cell subset counts (CD4 and CD8) at the indicated time points; b) specific proliferative responses of PBMC to rCD4, gp120 and recall antigens (tetanus and candida), before and one to two years after vaccination; and c) Anticlonotypic assay specific PBMC response to the injected cell lines or clones. The virological follow-up consisted of an assessment of HIV plasma viral load, two weeks after the first injection and thereafter approximately every three months.

Flowcytometry

Percentages of CD4 and CD8 and activation markers of T cells were assessed by flow cytometry analysis using FACS-Calibur™ (flow cytometer) and monoclonal antibodies specific for CD3, CD4 and CD8 from Becton-Dickinson Immuno-cytometry Systems, San Jose, Calif.

Analysis of T Cell Subsets and Activation Markers

One, two or three-color FACS analysis (FACScan™ (flow cytometer), Becton Dickinson Immunocytometry Systems, San Jose, Calif.) was performed on whole heparin-anti-coagulated blood within 3 hr after the blood collection. A mixture of one, two or three of the following monoclonal antibodies (MoAbs) conjugated with either fluorecein isothiocyanate (FITC), phycoerythrine (PE) or peridin chlorophyll protein (PerCP) directed against: CD3, CD4, CD8, HLA-DR, CD28, CD38, CD25 (Dako®, Glostrup, Denmark) or CTLA-4 (Pharmingen®) was used (Table 2 and data not shown). Expression of CTLA-4 was determined by intracytoplasmic staining with PE- or PerCP-conjugated anti-CTLA-4 [Leng (2001) Id ibid.]. After labeling the cells with MoAbs against CD4, CD8 and/or CD25, the cells are fixed with 1% paraformaldehyde, and membranes are permeabilized by incubation in PBS containing 0.1% saponin, 5% FCS and 1% human AB serum for 10 minutes. Staining and washing are performed once in PBS containing 0.1% saponin, 5% FCS and 1% human AB serum. Cells incubated with FITC, PE, or PerCP conjugated mouse IgG1/IgG2a (Dako®) serve as isotype controls. Lymphocytes are distinguished from monocytes on the basis of their forward versus side light scatter pattern. A minimum of 10,000 cells per sample was analyzed.

Determination of T Cell Antigen Specific Response by ELISPOT Assay

ELISPOT assay was performed essentially as described [Haslett et al. (2000) J. Infect. Dis. 181:1264-1272]. Briefly, 96-well plates (Millititer, Millipore®, Bedford, Mass., USA) were coated overnight at 4° C. with 10 µg/ml of the primary anti-IFN-γMoAbs (PharMigen, San Diego, Calif., USA). Following washing and blocking with RPMI containing 5% pooled human serum for 1 h at 37° C., PBMC (4×105) was added to each well in 200 µl together with no antigen, HIV gp120, gp41 (Protein Sciences Corp. Meriden, Minn., USA; 5 µg/ml), rCD4, tetanus toxoid and candida antigens, as well as baculovirus expressed control protein (5 µg/ml), or staphylococcal enterotoxin B (SEB; Toxin Technologies, Sarasota, Fla., USA; 10 ng/ml, positive control). In addition, PBMC were infected with vaccinia virus that was engineered to express the gene products HIV Gag, Pol, Lnv, or Nef (vac/gag, vac/pol, vac/env, and vac/nef, respectively) as the source of HIV antigen. The same strain of vaccinia, which contains an empty vector construct, also served as control (vac/ctrl). Following vaccinia infection, 2×105 PBMC were placed in each well. All cultures were performed in triplicate. After overnight culture at 37° C., plates were washed and incubated for 2 hours with a secondary biotinilated anti-IFN-γMoAb. Following further washing, an avidin-peroxidase complex was added (Vector Labs. Burlingame, Calif., USA), and the reaction developed with diamino-benzidine substrate (Research Genetics, Huntsville, Ala., USA). Resulting brown spots were counted with a stereomicroscope (Stemi-2000 stereo microscope, Carl Zeiss®, Inc., NY, USA) under magnification of 20-40×. Only spots with a fuzzy border and a brown color were counted. Each spot represents IFN-γ production by a single cell. Data was expressed as the number of spot-forming cells. ELISPOT assay for IFNγ is available from several sources, e.g. R&D Systems® Inc. This assay may also be performed with regards to IL-4, IL-b and TGFβ production.

Specificity Assay

Anti-CD4 T-cell specificity was performed prior to injection. Twenty thousand cells were cultured with 100,000 autologous APC (pulsed with rCD4). Cells were cultured for 3-5 days at 37° C. in a 5% $CO^2$ humidified incubator. $^3$H-thymidine uptake was measured as described previously. Positive cells (i.e., S.I. above 5) were used for TCV injection.

Cytotoxicity Assay

Seven days before the cytotoxic assay, fresh PBMC's were isolated from each patient. For target cell preparations, through negative selection, CD4+ enriched cells were isolated using CD8 coated magnetic dynabeads (DYNAL® A.S. Oslo, Norway). The cells were cultured 5 days with PHA (0.3 μg/ml) and rIL-2 (5-20 U/ml). On the day of the assay, $^{51}CrNa_2CrO_4$ (New England Nuclear, Boston, Mass., USA) was added to the culture (100 μCi/$10^6$ cells) and after one hour of incubation, the cells were washed with fresh culture medium. Effector cells (anti-CD4 CD8 enriched cells, see below) were mixed with samples of the total target cells at effector/target (E/T) ratios of 1:10, 1:50, 1:100 and 1:200 (Table 3A shows results from 1:100 ratio). After four hours of incubation, the $^{51}$Cr released from the lysed target cells was measured using a gamma counter (LKB Wallac Stockholm, Sweden, and 1282 Compugamm, Copenhagen, Denmark). Specific killing was calculated as the percentage of chromium released, as previously described [Zarling (1992) Id ibid.].

Quality Control

Before injection, every T cell vaccine was tested for mycoplasma, bacteria, fungi, endotoxin and virus content.

Example 1

TCV Open Trial

Anti-CD4 Autoimmunity

Twenty-three HIV-1 subtype B infected patients and twenty healthy Caucasian blood donors, as well as twenty HIV subtype C patients and eighteen African healthy controls were screened. These subjects were tested for T cell proliferation responses to recombinant human CD4 (rCD4), to recombinant gp120 (rgp120), to tetanus toxoid and to Candida. Proliferation responses were measured in stimulation index (S.I.) as described previously [Abulafia-Lapid, R. et al. (2003) *J. Autoimmun.* 20(4):121-9]. Responses of both HIV subtype B and subtype C patients to rCD4 were significantly higher 31/43 (72%) compared to healthy controls 8/38 (29%). Thus, the HIV patients showed a significantly enhanced T-cell response to CD4 (mean S.I. 3.8±2.1) compared to controls (mean S.I. 1.4±0.35; P=0.0001, data not shown) except for patients receiving TCV (Table 1). Thirteen patients from the 43 screened were selected for receiving TCV (8 subtype B and 5 subtype C) (Table 1). Patients enrolled responded to rCD4 (mean S.I. 4.15±0.35 and only 2 of 8 tested responded to rgp120).

T-Cell Vaccination

An open pilot study of T-cell vaccination against CD4 autoimmunity was carried out in 13 of the HIV patients (P1-P13), all of whom were receiving HAART (Table 1). Subjects P1 to P8 were Caucasian, and thus infected with subtype B virus, whereas subjects P9 to P13 were African, and thus infected with subtype C virus. The cells used for vaccines were derived from peripheral blood mononuclear cells, stimulated and expanded for 21 days (see Experimental Procedures). The CD4-reactive T cells were enriched in CD8 T cells, relative to the staffing population (Table 2) and manifested high IFNγ and low IL-10 expression, therefore representing an enriched T1 type population. Prior to the vaccination, the cells were fixed with 1.0% glutaraldehyde so as to kill them and inactivate any live viruses they could be harboring. In addition, no HIV particles were found in the supernatants of these cultures (Amplicor® (PCR analyzer), Hoffman-LaRoche, Basel, Switzerland). It is noteworthy that no virus was detectable after 21 days of in vitro culture in the T cells of patients with viral loads in the blood; patients P2, P3, P5 and P12 had plasma viral loads of 14,000, 1,500, 2,000 and 2,200 copies/μl respectively, and 5%, 11%, 19% and 19% of CD4 T cells, respectively, remained in the T-cell vaccine preparation. P6, despite having only 7% remaining CD4 T cells in the T-cell vaccine preparation, had plasma viral load of 37,000 copies/μl blood (Tables 1 and 2). Nevertheless, the T-cell cultures used for vaccination were free of virus even before fixation.

TABLE I

Clinical Features of HIV-1 subtypes B and C infected patients enrolled for TCV

| Subject # | Sex/Age | Subtype | Disease Duration (yrs) | Duration of HAART (yrs) | Viral load (copies/ml) | CD4 (cells/μl) | (%) | Proliferation (S.I.) rgp120 | rCD4 | Tetanus T. | Candida |
|---|---|---|---|---|---|---|---|---|---|---|---|
| P1 | M/63 | B | 11 | 2.3 | <400 | 348 | 21 | 1.6 | 4.2 | 5.7 | 6.5 |
| P2 | M/35 | B | 9 | 2 | 14,000 | 394 | 28 | 1 | 4.5 | 2.2 | 1.6 |
| P3 | M/36 | B | 10 | 2.3 | 1,500 | 327 | 26 | nd | 7 | 5.7 | 13.2 |
| P4 | M/55 | B | 5 | 1.8 | <400 | 289 | 29 | 1 | 2 | 5.6 | 2.0 |
| P5 | M/41 | B | 2 | 3.2 | 2,000 | 172 | 17 | 2.9 | 2 | 1.3 | nd |
| P6 | M/50 | B | 12 | 0.5 | 37,000 | 247 | 14 | 1 | 5.7 | 2.8 | 9.6 |
| P7 | M/40 | B | 13 | 2 | <400 | 388 | 23 | 1 | 7.8 | 15.1 | 24.0 |
| P8 | M/59 | B | 2 | 1.5 | <400 | 531 | 25 | 3.6 | 6.9 | 14 | 4.6 |
| P9 | M/51 | C | 3 | 3 | <400 | 473 | 29 | nd | 2.2 | 1 | nd |
| P10 | M/37 | C | 4 | 2.9 | <400 | 386 | 19 | nd | 2 | nd | nd |
| P11 | M/49 | C | 3 | 1.8 | <400 | 194 | 23 | nd | 2.8 | 1 | nd |
| P12 | M/38 | C | 5 | 3 | 2,200 | 229 | 17 | 1.4 | 4.9 | 1 | nd |
| P13 | F/29 | C | 2 | 2 | BD | 255 | 24 | 1.7 | 2 | 11.3 | nd |
| Median | 41 | | 5 | 2 | 2,200 | 327 | 23 | 1.2 | 4.4 | — | — |
| Mean | | | | | | | | 1.7 ± 0.9 | 4.15 ± 2. | — | — |

Features of Anti-CD4 Reactive T-Cells

The anti-CD4 reactive T-cells were further characterized for their cell surface markers and cytokine secretion profile. Anti-CD4 reactive T-cells were isolated from 8 patients (P1-P8) and compared to fresh PBMCs. Table 2 shows that CD4-reactive T-cells were highly activated as manifested by the increase of CD3/HLA-DR percentage (from 6-27% to 35-78%) following CD4 activation. The cells were also enriched with CD8 T-cell subsets relative to the PBMC, representing an enriched Th1-type population as seen by a high IFNγ and a low IL-4 cytokine expression (Table 2 and data not shown). As controls, cells were isolated from 2 of the 8 HIV-1 patients and cultured with either PHA and IL-2 for 14 days or cultured with only IL-2 for 7 days. Expression of IFNγ cytokine levels was found to be lower than anti-CD4 reactive T cells, ranging from 1,240 to 5,530 pg/ml (below 1000 pg/ml or below 300 pg/ml, respectively in both patients tested, data not shown).

In addition, cytotoxic activity measurements were done in 6 patients (P1-P6, Table 2). In this assay, anti-CD4 reactive T cells were used as effectors and added to autologous CD4+ enriched T-cell targets (as described in Experimental Procedures). The results suggest the presence of cytotoxic activity in all anti-CD4 reactive T cells tested, ranging between 10% to 67% above background (measured in percentage of chromium release).

PBMCs were isolated from healthy donors grown with PHA and IL-2 for 15 days and used as effectors, which were mixed with autologous CD4+ targets (data not shown) and tested in a cytotoxic assay as described above. 13% of cytotoxic activity was apparent. This result suggests that the elevated cytotoxic activity found in HIV-1 patients was mainly caused by the anti-CD4 reactive cells.

The autologous T-cell vaccine preparations were injected subcutaneously with about $10^7$ T cells in 1 ml of saline administered three or four times at intervals of two to six months. No clinical or laboratory side-effects were observed during the one year (P5 and P7) two years (P1, P2, P3, P4, P6) or several months (P8 received only 2 injections of TCV and all type C patients are still undergoing TCV), follow-up period. Nine of the 13 vaccinated subjects responded with increased levels (above 50%) of circulating CD4 T cells, compared to the mean levels of CD4 T cells observed during the two-year period preceding the T-cell vaccination (Table 3A). Among the subtype C patients, two patients (P9 and P11) manifested an increase in CD4 T-cell levels (above 50%). No decrease in CD4 cell levels was reported in all TCV patients. Furthermore, as can be seen in Table 3B, a spontaneous rise of CD4 levels was not observed in the control group of HIV infected patients that also received HAART and had a similar degree of HIV suppression during the same period of time.

Tables 3A and 3B: Peripheral Blood CD4 T-Cell Numbers and Viral Load

TABLE 3A

| | TCV treated HIV-1 patients | | | | |
|---|---|---|---|---|---|
| | CD4 cells/μl blood | | | HIV Plasma viral load (copies/ml) | |
| Patient number | *Pre-vaccination | **Post-vaccination | % Change | *Pre-vaccination | **Post-vaccination |
| P1 | 353 ± 100 | 600 | 70 | <400 | <400 |
| P2 | 413 ± 112 | 701 | 69 | 14,000 | 229,000 |
| P3 | 290 ± 52 | 523 | 80 | 1,500 | 1,490 |
| P4 | 275 ± 41 | 512 | 86 | <400 | <400 |
| P5 | 187 ± 54 | 277 | 48 | 2,000 | <400 |

TABLE 2

Cell surface markers, cytokine expression and cytotoxicity of anti-CD4 reactive T cells.

| | Fresh PBMC | | | T Cell Vaccine | | | | | |
|---|---|---|---|---|---|---|---|---|---|
| Patient | CD4 (%) | CD8 (%) | CD3/HLA-DR (%) | CD4 (%) | CD8 (%) | CD3/HLA-DR (%) | IFNγ (pg/ml) | IL10 (pg/ml) | CTL* (%) |
| P1 | 28 | 27 | 12 | 15 | 53 | 66 | 3090 | 34 | 67 |
| P2 | 19 | 52 | 21 | 5 | 92 | 68 | 2560 | 82 | 24 |
| P3 | 26 | 56 | 12 | 11 | 73 | 67 | 1390 | 78 | 60 |
| P4 | 30 | 43 | 14 | 27 | 61 | 90 | 1760 | 170 | 17 |
| P5 | 16 | 39 | 18 | 19 | 70 | nd | 5530 | 38 | 10 |
| P6 | 14 | 40 | 27 | 7 | 88 | 35 | 1240 | 110 | 22 |
| P7 | 23 | 55 | 6 | 9 | 86 | 78 | nd | nd | nd |
| P8 | 28 | 37 | 16.7 | nd | nd | 51.5 | nd | nd | nd |
| P9 | nd | nd | nd | 13 | 65 | nd | nd | nd | nd |
| P10 | nd | nd | nd | 14 | 43 | nd | nd | nd | nd |
| P11 | 36 | 27 | nd | 9 | 89 | nd | nd | nd | nd |
| P12 | nd | nd | nd | 19 | 62 | nd | nd | nd | nd |
| P13 | 27 | 20 | nd | 15 | 60 | nd | nd | nd | nd | nd = not determined

*% of lysis of autologous CD4+ T cell targets

TABLE 3A-continued

TCV treated HIV-1 patients

| Patient number | CD4 cells/μl blood | | | HIV Plasma viral load (copies/ml) | |
|---|---|---|---|---|---|
| | *Pre-vaccination | **Post-vaccination | % Change | *Pre-vaccination | **Post-vaccination |
| P6 | 252 ± 106 | 385 | 52 | 37,000 | 5,690 |
| P7 | 237 ± 96 | 450 | 89 | <400 | <400 |
| P8 | 402 ± 180 | 926 | 130 | <400 | <400 |
| P9 | 422 ± 81 | 639 | 51 | <400 | <400 |
| P10 | 413 ± 92 | 440 | 6.5 | <400 | <400 |
| P11 | 204 ± 38 | 409 | 100 | <400 | <400 |
| P12 | 165 ± 50 | 199 | 20 | 9,940 | 34,200 |
| P13 | 290 ± 27 | | | <400 | <400 |

TABLE 3B

Untreated HIV-1 subjects

| Patient number | CD4 cells/μl blood | | | HIV Plasma viral load (copies/ml) | |
|---|---|---|---|---|---|
| | *Pre-vaccination | **Post-vaccination | % Change | *Pre-vaccination | **Post-vaccination |
| CP1 | 142 ± 29 | 167 | 18 | 5130 | 958 |
| CP2 | 202 ± 43 | 256 | 27 | 6930 | 6890 |
| CP3 | 136 ± 33 | 220 | 61 | <400 | <400 |
| CP4 | 190 ± 52 | 224 | 18 | 3790 | <400 |
| CP5 | 198 ± 40 | 279 | 40 | <400 | <400 |
| CP6 | 153 ± 41 | 235 | 53 | 3890 | 1220 |
| CP7 | 311 ± 124 | 282 | −9 | 8300 | 5830 |

*Mean of 2 years before vaccination.
**Measured after 1 year in patients P5 & P7, after 2 years in patients P1–P4, P6, and less than 1 year in the rest of patients.

In addition, among the subtype B patients, no increase in the plasma viral loads were detected after one year in patients P5 and P7, after two years in patients P1, P3, P4 and P6, and after half a year (two injections) in patient P8 following TCV. In fact, patients P5 and P6 manifested a significant decrease from 2,000 copies/μl to below detection, and from 37,000 to 5,600 copies/μl, respectively (Table 3A). Patient P2 is the only exception; however, his viral load was unusually unstable from the beginning, with ups and downs which continued after TCV. In addition, his CD4 cell count improved significantly during the two years following TCV. Among the subtype C patients, P9, P10, P11 and P13 remained below detection levels during a period of up to one year. Patient P12 manifested increase in the viral load (34,200) (was not tolerating HAART); however, after his HAART therapy was recently altered, his viral load became below detection. In five of the 7 patients that completed the TCV (P1, P2, P3, P4 and P6), the inventors were able to test the T-cell responses to rCD4 two years after vaccination. A fall in the anti-CD4 response was observed in four patients, and a rise in the T-cell response to tetanus toxoid was seen in two of them (data not shown). Taken together, T-cell vaccination using autologous T cells as a vaccine was associated with a decrease in anti-CD4 autoimmunity and a concomitant increase in CD4 T-cell numbers, in certain subjects. P9 to P13 were evaluated before receiving all the boosters.

Example 2

The Protocol

The protocol is intended for the wide scale treatment of AIDS patients, with respect to their immunodeficiency triggered by the HIV infection. Thus, the HIV-infected patients are treated with the TCV presented herein, in particular for patients where HIV is suppressed by antiretroviral treatment (HAART), and/or patients that present low CD4 counts. This protocol also includes the evaluation of the efficacy of the TCV treatment, which is essential when applying this kind of therapy. A summary of the protocol is presented in FIG. 4.

Patients

Both male and female patients (age 18-65 years) tested positive for HIV through ELISA (Abbot, USA) and confirmed by Western Blot, may be enrolled from any AIDS or Infectious Disease Center in Israel or abroad. Children may also be enrolled in the protocol, if they show signs of autoimmune disease, i.e., low CD4+ cell count and/or reactivity to CD4 molecule.

Protocol Inclusion Criteria:

a) Patients with CD4 cell counts ranging from 150-250 mm$^3$, 250-350 mm$^3$ (below 150 mm$^3$ if possible) and treatment with HAART for at least 6 months. Patients with CD4 cell counts above 350 mm$^3$ are evaluated and accepted or not on a per case basis. Alternatively, HAART interruption, or naïve patients can be enrolled.

b) Positive cell proliferation assay to CD4 molecule.

c) No change of antiretroviral treatment for over 6 months prior to the vaccination.

Protocol Exclusion Criteria:

a) Any concomitant medication with immunosuppressive or anti-neoplastic drugs, as well as chronic systemic glucocorticoid therapy;

b) Pregnancy or lactation;

c) Clinically relevant liver disease (AST and/or ALT >2.5× upper limit of normal range, or total bilirubin >3.5 mg/dl);

d) Serum creatinine >1.8 mg/dl or creatinine clearance <30 ml/min;

e) Cancer;

f) Legal incapacity or other circumstances rendering the patient unable to understand the nature, scope and possible consequences of the treatment;

g) Evidence of an uncooperative attitude.

The protocol starts with the screening of patients with respect to exclusion and inclusion criteria of the study, following usual clinical procedures. Patients found suitable for inclusion are asked for written informed consent and are enrolled in the protocol. On the first visit, the patients are requested to sign a written informed consent, and to fill out the information concerning demographics, medical history and pre-existing diseases, as well as previous and concomitant treatment. The following laboratory tests are required:

Blood T cell subsets: CD3, CD4, CD8, CD4/CD8, CD45RO, CD45RA, CD28;

Plasma HIV-1 RNA load;

FACS analysis for activation markers: HLA-DR, CD8/CD38, CD25, CTLA-4 and apoptosis;

Specific anti-CD4 immunity: proliferation, ELISPOT (for cytokine release pattern) and humoral tests;

Skin tests for delayed hypersensitivity (DTH) to recall antigens;

Specific immune response (proliferation and ELISPOT) to HIV antigens (particularly gp120, gp41);

Specific immune response (proliferation) to recall antigens such as tetanus toxoid, Candida, influenza, etc.

The time line of all the tests requested from the patients is summarized in Table 4. Please note that some of the Laboratory tests performed in the first phase of the protocol are also performed as part of the follow up phase.

dida and influenza higher than the baseline (before TCV) indicate improvement in the immune responsiveness to other infections implying towards strengthening the immune system.

iii) Cytotoxicity assay: Anti-CD4 reactive T-cells are isolated and tested for cytotoxic activity against autologous CD4 targets.

TABLE 4

Time line of protocol and tests

| Test No. | | Day 0 | Month 3 | Month 6 | Month 9 | Month 12 | Month 18 | Month 24 |
|---|---|---|---|---|---|---|---|---|
| 1 | Informed consent | X | | | | | | |
| 2 | Physical examination and clinical follow-up | X | X | X | X | X | X | X |
| 3 | T cell subsets-CD4, CD8, CD4/CD8 ratio | X | X | X | X | X | X | X |
| 4 | Plasma HIV-1 RNA load | X | X | X | X | X | X | X |
| 5 | Activation markers: HLA-DR, CD8/CD38, CD25, CTLA-4 CD28 | X | | X | | X | | X |
| 6 | Specific anti-CD4 immunity: cellular and humoral + Regulatory cells | X | | | | X | | X |
| 7 | Skin tests for delayed hypersensitivity (DTH) to recall antigens | X | | | | X | | X |
| 8 | Specific immune response(proliferation and ELISPOT) to HIV antigens(gp120, gp41) | X | | | | X | | X |
| 9 | Specific immune response(proliferation and ELISPOT) to recall antigens | X | | | | X | | X |
| 10 | Anti clonotipic test (anti TCV cells) | | | | | X | | X |
| 11 | T cell vaccination | X | X | X | X | X | X | X |

Tables 3 and 4 are performed two and four weeks following each TCV injection. Regarding the timing of the T cell vaccination, in optimal conditions a booster should be preferably administered after 3 and 6 months on the first year, then after 12 and 18 months on the second year. Boosters at 9 and 24 months are optional. Booster administration should always be preceded by clinical evaluation and followed up by the professional personnel in charge.

Clinical follow-up: Viral load and plasma CD4 cell counts (see above).

Immunological Follow-Up:

i) Anti-clonotypic assay: PBMC are isolated as described above and cultured in the presence of irradiated anti-CD4 T-cells (those used for injection) in a proliferation assay setting. Culture ratio is 100,000 PBMC and 25,000 irradiated anti-CD4 cells. Five days following culture, cells are labeled with $^3$H-thymidine (overnight) and assayed as described. Results of an S.I. >2 indicates anti-CD4 clonotypic activity probably induced by TCV.

ii) Anti-CD4 autoimmunity: Proliferation assay using fresh PBMCs is accomplished. Antigens are rCD4, rgp120, and recall antigens, as described previously. An S.I. >2 indicates positive response. Positive responses to rCD4 mean ongoing autoimmunity against CD4 (more TCV injection has to be considered). Responses against recall antigens such as can- Most importantly, in order to keep the autoimmune process in remission, booster vaccines should be administered to the patient approximately every two years, under the supervision of the clinician in charge.

The invention claimed is:

1. A method of preparing a population of autologous T-cells enriched with inactivated CD8+ cells that are reactive to CD4+ cells, said method consisting of the steps of:
   a) Obtaining peripheral mononuclear blood cells (PMBC) from said patient;
   b) Culturing said autologous cells in the presence of a nonspecific stimulating factor;
   c) Expanding said autologous cells in the presence of IL-2, wherein said IL-2 is provided at 5-20 U/ml;
   d) Culturing said expanded autologous cells in the presence of irradiated CD4-pulsed antigen presenting cells (APCs);
   e) Inactivating said autologous cells in the presence of an inactivating factor;
   f) Washing said autologous cells and resuspending the same in injection-grade saline solution; and
   g) Optionally freezing aliquots of between $10^6$-$10^8$ cells in liquid nitrogen.

2. A method of preparing a substantially pure cell population enriched with inactivated CDS+ cells that are reactive to CD4+ cells, said method consisting of the method of claim 1, further comprising the step of repeating step (d) for between 4 to 8 times.

3. The method of claim 1, wherein the inactivated CD8+ cells are inactivated with a fixation solution.

4. The method of claim 3, wherein the fixation solution is glutaraldehyde.

* * * * *